(12) United States Patent
Maywald et al.

(10) Patent No.: US 6,392,058 B1
(45) Date of Patent: May 21, 2002

(54) METHOD FOR PRODUCING 1-SUBSTITUTED 5-HYDROXYPYRAZOLES

(75) Inventors: Volker Maywald, Ludwigshafen; Adrian Steinmetz, Mannheim; Michael Rack, Heidelberg; Norbert Götz, Worms; Roland Götz, Neulessheim; Jochem Henkelmann, Mannheim; Heike Becker, Limburgerhof; Juan Jose Aiscar Bayeto, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/856,201
(22) PCT Filed: Nov. 6, 1999
(86) PCT No.: PCT/EP99/08516
  § 371 Date: May 17, 2001
  § 102(e) Date: May 17, 2001
(87) PCT Pub. No.: WO00/31042
  PCT Pub. Date: Jun. 2, 2000

(30) Foreign Application Priority Data
Nov. 19, 1998 (DE) .......... 198 53 502

(51) Int. Cl.[7] ............................. C07D 231/20
(52) U.S. Cl. .................. 548/368.1; 548/370.4
(58) Field of Search ............ 548/368.1, 370.4

(56) References Cited

U.S. PATENT DOCUMENTS

| | | |
|---|---|---|
| 4,643,757 A | 2/1987 | Baba |
| 4,744,815 A | 5/1988 | Baba |
| 5,543,568 A | 8/1996 | Henkelmann |
| 5,607,898 A | 3/1997 | Nakamura |
| 5,631,210 A | 5/1997 | Tseng |
| 5,663,365 A | 9/1997 | Yamamoto |
| 5,723,408 A | 3/1998 | Shibata |
| 5,808,092 A | 9/1998 | Mizutare |
| 5,846,907 A | 12/1998 | von Deyn |
| 5,863,866 A | 1/1999 | Takashima |
| 5,985,799 A | 11/1999 | Tseng |

FOREIGN PATENT DOCUMENTS

EP     240 001     10/1987

(List continued on next page.)

OTHER PUBLICATIONS

Derwent 97–100145/09 (1997).
Journal Fur Praktische Chemie, Band 313, 1971,115–128 Dorn et al. Journal Fur Praktische Chemie, Band 313, 1971, 1118–1124 Dorn et al.
Chemische Ber. 109,261–267 (1976) Einige Produkte aus 1–Alkyl–5–hydroxy–3–py4azolcarbonsaure methylestern Sucrow et al.

*Primary Examiner*—Robert W. Ramsuer
(74) *Attorney, Agent, or Firm*—Keil & Weinkauf

(57) ABSTRACT

The invention relates to a process for preparing 1-substituted 5- and/or 3-hydroxypyrazoles of the formulae I and II

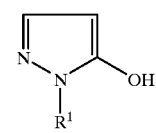

I

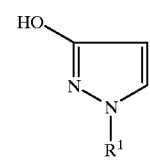

II in which $R^1$ is $C_1$–$C_6$-alkyl, $C_2$–$C_6$-alkenyl, $C_2$–$C_6$-alkynyl, $C_3$–$C_6$-cycloalkyl or $C_1$–$C_4$-alkoxy, where these groups may be substituted by halogen, $C_1$–$C_4$-alkoxy, phenoxy, $C_1$–$C_6$-alkoxycarbonyl, $C_1$–$C_6$-alkylthiocarbonyl or by a cyclic ring system having 3–14 ring atoms, which comprises reacting an alkyl 3-alkoxyacrylate of the formula III

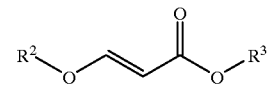

III in which $R^2$, $R^3$ independently of one another are $C_1$–$C_6$-alkyl or $C_3$–$C_6$-cycloalkyl with a hydrazine of the formula IV

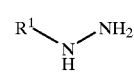

IV in which $R^1$ is as defined above a) at a pH of 6–11 to give 5-hydroxypyrazoles of the formula I or b) at a pH of 11–14 to give 3-hydroxypyrazoles of the formula II.

13 Claims, No Drawings

FOREIGN PATENT DOCUMENTS

| | | |
|---|---|---|
| EP | 587 072 | 3/1994 |
| EP | 818 455 | 1/1998 |
| EP | 837058 | 4/1998 |
| EP | 970 956 | 1/2000 |
| JP | 58-140073 | 8/1983 |
| JP | 570149974 | 8/1983 |
| JP | 58-174369 | 10/1983 |
| JP | 60-51175 | 3/1985 |
| JP | 61-189271 | 8/1986 |
| JP | 61-229852 | 10/1986 |
| JP | 61-268659 | 11/1986 |
| JP | 61-257974 | 11/1987 |
| JP | 06166666 | 6/1994 |
| WO | 96/25412 | 8/1996 |
| WO | 96/26206 | 8/1996 |
| WO | 96-30368 | 10/1996 |
| WO | 96/31507 | 10/1996 |
| WO | 97/01550 | 1/1997 |
| WO | 97/08164 | 3/1997 |
| WO | 97/12885 | 4/1997 |
| WO | 97/19087 | 5/1997 |
| WO | 97/23135 | 7/1997 |
| WO | 00/31042 | 6/2000 |

METHOD FOR PRODUCING 1-SUBSTITUTED 5-HYDROXYPYRAZOLES

This application is a 371 of PCT/EP99/08516 filed Nov. 6, 1994.

The present invention relates to a process for preparing 1-substituted 5- and/or 3-hydroxypyrazoles of the formulae I and II, respectively

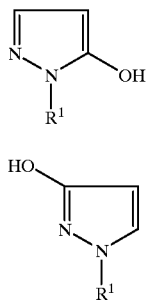

in which $R^1$ is $C_1$–$C_6$-alkyl, $C_2$–$C_6$-alkenyl, $C_2$–$C_6$-alkynyl, $C_3$–$C_6$-cycloalkyl or $C_1$–$C_4$-alkoxy, where these groups may be substituted by halogen, $C_1$–$C_4$-alkoxy, phenoxy, $C_1$–$C_6$-alkoxycarbonyl, $C_1$–$C_6$-alkylthiocarbonyl or by a cyclic ring system having 3–14 ring atoms, which comprises [lacuna] 1-Substituted 5- and 3-hydroxypyrazoles are used as intermediates for preparing pharmaceutics and crop protection agents, in particular herbicides, and are disclosed, for example, in WO96/26206, WO 97/23135, WO 97/19087, U.S. Pat. No. 5,631,210, WO 97/12885, WO 97/08164, ZA 9510980, WO 97/01550, WO 96/31507, WO 96/30368, WO 96/25412 and U.S. Pat. No. 5,663,365.

Processes for their preparation are therefore of interest.

To date, the following syntheses are known as processes for preparing lower 1-alkyl-5-hydroxypyrazoles:

1. a preparation where 2-methyl-1-(p-toluenesulfonyl)-3-pyrazolidone or 2-methyl-1-1-acetyl-pyrazolidone [sic] is hydrolyzed (J. Prakt. Chem. 313 (1971), 115–128 and J. Prakt. Chem. 313 (1971), 1118–1124).
2. a variant in which alkyl 5-hydroxy-1-alkylpyrazole-4-carboxylate is synthesized by cyclization of a dialkyl alkoxymethylenemalonate with lower alkylhydrazines, an aqueous solution of mineral acid is subsequently added to this reaction product and hydrolysis and decarboxylation are carried out simultaneously (see JP 61257974, JP 60051175, JP 58174369, JP 58140073 and JP 58140074 and also U.S. Pat. No. 4,643,757).
3. a synthesis in which ethyl propiolate is reacted with methylhydrazine to give 5-hydroxy-1-methylpyrazole (Annalen 686 (1965), 134–144).
4. a synthesis route in which 3-hydrazinopropionic esters, which are formed by addition of hydrazine to acrylic esters, are reacted with aldehydes to give the corresponding hydrazones, which are subsequently cyclized (see JP 06166666, JP 61229852 and JP 61268659 and also EP 240001).
5. a synthesis variant in which a 5-hydroxy-1-methylpyrazole-3-carboxylic acid is cleaved thermally (Chem. Ber. 109 (1976), 261).
6. a process in which 3-alkoxyacrylic esters are reacted with methylhydrazine and ethylhydrazine to give 1-methyl-5-hydroxypyrazole and 1-ethyl-5-hydroxypyrazole, respectively (see JP 189 271/86, EP-A-837 058).
7. a process in which 2-haloacrylic esters are reacted with hydrazine derivatives to give 1-substituted 3-hydroxypyrazoles (see U.S. Pat. No. 5,663,365).

The process of the 1st synthesis route mentioned above entails several steps and is complicated. Introduction and removal of a protecting group is awkward, means an additional number of steps and reduces the yield.

The 2nd preparation possibility entails several steps; moreover, in addition to the 1-alkyl-5-hydroxypyrazoles, the regioisomers of the target compound are formed at the same time, and they have to be separated off from the target compounds in a complicated procedure. Furthermore, the synthesis is associated with a poor C yield since a C4 building block is employed from which, at the end of the process, a carbon atom has to be cleaved off again.

In the 3rd synthesis variant, which describes only the preparation of 1-methyl-5-hydroxypyrazole, it is unavoidable to employ highly hyperstoichiometric amounts of methylhydrazine, thus rendering the process uneconomical. In addition, the isomer 3-hydroxy-1-methylpyrazole, which is also formed, has to be separated off from 1-methyl-5-hydroxypyrazole in a complicated procedure during purification. Furthermore, owing to the high cost of propiolic ester, this process is uneconomical.

The process of the 4th alternative entails several steps and is complicated. The last step of the complex process affords only poor yields and a large number of byproducts.

The thermal cleavage of the 5th synthesis route requires a high temperature, and the yield of 6% is very low.

The 6th synthesis route, which describes only the preparation of 1-methyl-5-hydroxypyrazole, uses 3-alkoxyacrylic esters which are difficult to prepare and are expensive. The preparation of 3-alkoxyacrylic esters is carried out by reaction of methanol with expensive propiolic esters (Tetrahedron Lett. 24 (1983), 5209, J. Org. Chem. 45 (1980), 48, Chem. Ber. 99 (1966), 450, Chem. Lett. 9 (1996), 727–728), by reacting α,α-dichlorodiethyl ether, which is expensive and difficult to synthesize, with bromoacetic esters (Zh. Org. Khim. 22 (1986), 738), by reaction of bromoacetic esters with trialkyl formates (Bull. Soc. Chim. France N 1–2 (1983), 41–45) and by elimination of methanol from 3,3-dialkoxypropionic esters (DE 3701113) (obtainable by reacting the expensive methyl propiolate with methanol (J. Org. Chem. 41 (1976), 3765)), by reacting 3-N-acetyl-N-alkyl-3-methoxypropionic esters with methanol (J. Org. Chem. 50 (1985), 4157–4160, JP 60–156643), by reacting acrylic esters with alkylamines and acetic anhydride (J. Org. Chem. 50 (1985), 4157–4160), by reacting ketene with trialkyl orthoformate (DK 158462), by palladium- and simultaneously copper-catalyzed reaction of acrylic esters with methanol (DE 4100178.8), by reaction of trichloroacetyl chloride with vinyl ethyl ether (Synthesis 4 (1988), 274), by reacting α,α,α-trichloro-β-methoxybutene-2-one with methanol (Synthesis 4 (1988), 274) and by reacting the sodium salts of 3-hydroxyacrylic esters with alcohols (DB 3641605). The fact that the 3-alkoxyacrylic esters are difficult to obtain thus renders the synthesis according to 6 uneconomical. Moreover, JP 189 271/86 only describes the isolation of the 5-hydroxy-1-methylpyrazole as the hydrochloride, but no details are given for the isolation and purification of the free base. Efforts to apply the reaction conditions described in JP 189 271/86 and to isolate the free base result in only very poor yields which are uneconomical for a preparation of hydroxypyrazoles on an industrial scale.

The 7th synthesis route has the disadvantage that only 3-hydroxypyrazoles can be prepared, and no 5-hydroxypyrazoles. Consequently, these synthesis routes are not satisfactory as economical and efficient processes for preparing 1-substituted 5- and 3-hydroxypyrazoles.

Furthermore, there is no process known from the prior art which permits preparation of both the 1-substituted 5- and the 3-hydroxypyrazole by simple variation of the process parameters.

Moreover, there is no process known from the prior art which leads to the desired 1-substituted 5- and 3-hydroxypyrazoles from simple starting materials such as an alkyl vinyl ether.

It is an object of the present invention to provide a process which allows the preparation of 1-substituted 5-hydroxypyrazoles and/or 3-hydroxypyrazoles in [sic] by changing the process parameters.

It is another object of the present invention to provide a process for preparing 1-substituted 5-hydroxypyrazoles and/or 3-hydroxypyrazoles from easily obtainable starting materials which does not have the abovementioned disadvantages of the prior art processes.

We have found that this object is achieved by the process according to the invention for preparing 1-substituted 5- and/or 3-hydroxypyrazoles of the formulae I and II

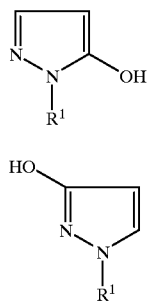

in which $R^1$ is $C_1$–$C_6$-alkyl, $C_2$–$C_6$-alkenyl, $C_2$–$C_6$-alkynyl, $C_3$–$C_6$-cycloalkyl, $C_1$–$C_4$-alkoxy or phenoxy, where these groups may be substituted by halogen, $C_1$–$C_4$-alkoxy, $C_1$–$C_6$-alkoxycarbonyl, $C_1$–$C_6$-alkylthiocarbonyl or by a cyclic ring system having 3–14 ring atoms, by reacting an alkyl 3-alkoxyacrylate of the formula III

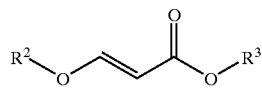

in which $R^2$, $R^3$ independently of one another are $C_1$–$C_6$-alkyl or $C_3$–$C_6$-cycloalkyl with a hydrazine of the formula IV

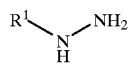

in which $R^1$ is as defined above
a) at a pH of 6–11 to give 5-hydroxypyrazoles of the formula I or
b) at a pH of 11–14 to give 3-hydroxypyrazoles of the formula II.

Moreover, we have found a process starting from easily obtainable alkyl vinyl ethers for preparing the alkyl 3-alkoxyacrylate of the formula III by reacting c) an alkyl vinyl ether of the formula V

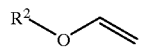

in which $R^2$ is as defined in claim 1 with phosgene VIa, "diphosgene" VIb or "triphosgene" VIc

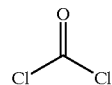

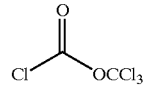

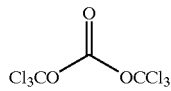

to give an acyl chloride of the formula VII

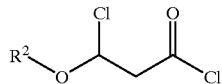

d) converting this by elimination of hydrogen chloride into the corresponding 3-alkoxyacryloyl chloride of the formula VIII

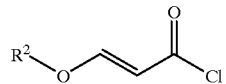

and
e) esterifying this with an alcohol of the formula IX

in which $R^3$ is as defined in claim 1 to give the corresponding alkyl 3-alkoxyacrylate of the formula III.

Surprising and novel in the process according to the invention are the facts that 5- or 3-hydroxypyrazoles of the formulae I and II, respectively, can be prepared selectively by appropriate choice of the reaction conditions, and that easily obtainable starting materials can be employed.

Preferred embodiments of the process according to the invention are shown in the subclaims and in the description below.

Step a):

The reaction of the alkyl 3-alkoxyacrylates of the formula III with hydrazines of the formula IV to give the 1-substituted 5-hydroxypyrazoles is generally carried out by initially charging one of the two reaction participants in a suitable solvent and metering in the second reaction participant at from −30° C. to 100° C. By addition of a base, the pH is kept at 7–11, preferably 8–11, particularly preferably 9–11. Suitable bases are, for example, alkali metal and alkaline earth metal hydroxides, such as sodium hydroxide and potassium hydroxide, and also tertiary amines.

Preferred bases are alkali metal and alkaline earth metal hydroxides, such as sodium hydroxide and potassium hydroxide. The molar ratio of alkyl 3-alkoxyacrylate III to hydrazine IV is from 1:1 to 1:10, preferably from 1:1 to 1:8. This ratio can be reduced from 1:10 to 1:1 by addition of bases.

According to a preferred procedure, only the solvent is initially charged, and the hydrazine IV and the alkyl 3-alkoxyacrylate III are added simultaneously dropwise over a period of from 10 min to 10 h, preferably 1–4 h. The particular advantage of this parallel addition consists in the fact that this allows the pH of the reaction mixture to be kept constant at approximately 10, without addition of a base being required. The maintenance of this pH, in turn, is essential for the regioselectivity of the reaction. When a pH of 10, for example, is maintained, it is possible to obtain regioisomer ratios I:II of more than 300:1.

Moreover, it has been found to be favorable to reduce the temperature after a certain reaction time and to allow the reaction to go to completion at a correspondingly lower temperature.

Suitable solvents or diluents are, for example, water, aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, alcohols, such as methanol and ethanol, and also ethers, such as diethyl ether, diisopropyl ether, tert-butyl methyl ether, dioxane, anisole and tetrahydrofuran, and nitriles, such as acetonitrile and propionitrile. It is of course also possible to use mixtures of the abovementioned solvents.

Preferred solvents are, for example, water, alcohols, such as methanol and ethanol, ethers, such as diethyl ether, diisopropyl ether, tert-butyl methyl ether, dioxane, anisole, diethylene glycol dialkyl ethers and tetrahydrofuran, and mixtures of these.

The hydrazines IV can be employed both neat and in the form of their aqueous solutions, some of which are commercially available.

Step b):

The reaction of the alkyl 3-alkoxyacrylates III with hydrazines IV to give the 1-substituted 3-hydroxypyrazoles II is preferably carried out by initially charging the hydrazine IV in a suitable solvent and metering in the alkyl 3-alkoxyacrylate VIII at from −30° C. to 100° C., preferably at 10–40° C., over a period of from 10 min to 10 h, preferably 1–4 h. During this addition, the pH is kept between 11 and 14, preferably at 12–13, in particular at 12, by addition of a base. By adjusting the pH to the last-mentioned values, it is possible to obtain the 1-substituted 3-hydroxypyrazoles II in high regioselectivity. Suitable bases are alkali metal and alkaline earth metal hydroxides, such as sodium hydroxide and potassium hydroxide, and tertiary amines. Preferred bases are alkali metal and alkaline earth metal hydroxides. Suitable solvents are those mentioned in step a).

Step c):

The overall process according to the invention starts with alkyl vinyl ethers of the formula V which are initially reacted at from −78° C. to 100° C., preferably from -10° C. to 80° C., in particular from 20° C. to 60° C., with an acyl chloride of the formula VIa, VIb or VIc, to give the corresponding acyl chloride of the formula VII.

The reaction can be carried out without using solvents or diluents if the reaction partners are liquid at the reaction temperature. However, it is also possible to carry out the reaction in an aprotic solvent or diluent.

Suitable solvents or diluents are, for example, aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, and also ethers, such as diethyl ether, diisopropyl ether, tert-butyl methyl ether, dioxane, anisole and tetrahydrofuran, and nitrites, such as acetonitrile and propionitrile. It is of course also possible to use mixtures of the abovementioned solvents.

Particularly preferably, the reaction is carried out in the absence of a solvent, or in aromatic hydrocarbons such as toluene as solvent.

The reaction partners V and VI are generally reacted with each other in a ratio of from 0.1:1 to 1:1 mol of V/VIa, VIb or VIc, preferably from 0.2:1 to 0.8:1 mol of V/VIa, VIb or VIc, in particular from 0.4:1 to 0.6:1 mol of V/VIa, VIb or VIc.

Since both the halides VI and the acyl chloride VII which is formed are unstable toward moisture, it is recommended to carry out the reaction under exclusion of water, preferably under an atmosphere of protective gas (nitrogen or another inert gas).

In the case of the reaction of V with VIb or VIc, it may be advantageous to accelerate the reaction by addition of catalytic amounts of a tertiary amine, such as triethylamine or pyridine.

Step d):

At 30–80° C., the resulting acyl chloride VII eliminates hydrogen chloride (HCl), giving the corresponding 3-alkoxyacryloyl chloride VIII.

For this step of the reaction, it may be advantageous to remove the hydrogen chloride which is formed from the reaction volume, by applying slightly reduced pressure or by passing inert gas through the reaction mixture or the reaction vessel, thus removing the hydrogen chloride which is formed.

The excess chloride of the formula VIa, VIb or VIc can be recycled into the synthesis and has to be removed in any case for the isolation of the pure product of value. This also applies to any catalysts which may have been added.

The resulting crude 3-alkoxyacryloyl chlorides VIII can be isolated in pure form by distillation or rectification.

However, they can also be converted directly, without further purification, into the corresponding alkyl 3-alkoxyacrylates III.

Step e):

The acyl chlorides VIII are generally esterified by adding the alcohol IX dropwise to the acyl chloride VIII, at from −20 to 80° C., preferably at 0–50° C., over a period of 0.5–8 h, preferably 1–6 h, and purifying the resulting alkyl 3-alkoxyacrylate III by continuous or batchwise distillation or rectification.

However, it is also possible to carry out the reaction in an aprotic solvent or diluent. Suitable solvents or diluents are, for example, aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, and also ethers, such as diethyl ether, diisopropyl ether, tert-butyl methyl ether, dioxane, anisole and tetrahydrofuran, and nitriles, such as acetonitrile and propionitrile. It is of course also possible to use mixtures of the abovementioned solvents.

It is recommended to carry out the reaction in the presence of hydrogen chloride-binding reagents, such as, for example, pyridine. It is of course also possible to use the last-mentioned reagents as solvents.

With respect to the intended use of the 1-substituted 5- and/or 3-hydroxypyrazoles of the formulae I and II, the following radicals are suitable substituents:

$R^1$ $C_1$–$C_4$-alkyl, such as methyl, ethyl, n-propyl, 1-methylethyl, butyl, 1-methylpropyl, 2-methylpropyl and 1,1-dimethylethyl;

$C_1$–$C_6$-alkyl, such as $C_1$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-thylbutyl, 2-ethylbutyl, 1,1,2-trimethylpropyl, 1-ethyl-1-methylpropyl and 1-ethyl-3-methylpropyl;

in particular methyl, ethyl, 1-methylethyl, 1-methylpropyl, 2-methylpropyl, 1,1-dimethylethyl and 1,1-dimethylpropyl;

$C_2$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3 pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 1-methyl-2-propenyl, 1-methyl-2-butenyl, 1,1-dimethyl-2-propenyl and 1,1-dimethyl-2-butenyl;

$C_2$–$C_6$-alkynyl, such as propargyl, 2-butynyl, 3-butenyl [sic], 2-pentynyl, 3-pentynyl, 4-pentynyl, 1-methyl-3-butynyl, 2-methyl-3-butynyl, 1-methyl-2-butynyl, 1,1-dimethyl-2 propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

$C_3$–$C_6$-cycloalkyl, such as, for example, cyclopropyl, cyclobutyl, cyclopentyl and cyclohexyl, in particular cyclopropyl and cyclohexyl;

$C_1$–$C_4$-alkoxy, such as methoxy, ethoxy, n-propoxy, 1-methylethoxy, n-butoxy, 1-methylpropoxy, 2-methylpropoxy and 1,1-dimethylethoxy, in particular $C_1$–$C_3$-alkoxy, such as methoxy, ethoxy, isopropoxy;

where these groups may be unsubstituted or substituted by one to five halogen atoms, such as fluorine, chlorine, bromine and iodine, preferably fluorine and chlorine, $C_1$–$C_4$-alkoxy, phenoxy, $C_1$–$C_6$-alkoxycarbonyl, $C_1$–$C_6$-alkylthiocarbonyl or a cyclic ring system having 3–14 ring atoms, where the substituents are as defined below:

$C_1$–$C_6$-alkoxycarbonyl, such as methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl, in particular methoxycarbonyl;

$C_1$–$C_6$-alkylthiocarbonyl, such as methylthiocarbonyl, ethylthiocarbonyl, n-propylthiocarbonyl, in particular methylthiocarbonyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

A cyclic ring system having 3–14 ring atoms means, for example, the following groups: $C_3$–$C_{14}$-cycloalkyl, $C_3$–$C_{14}$-cycloalkenyl, aromatic groups, such as phenyl, naphthyl, and their partially hydrogenated derivatives. The cyclic ring systems may furthermore represent heterocyclic ring systems in which one, two or three carbon atoms may be replaced by heteroatoms, such as, for example, O, N, S. In principle, the cyclic ring systems may be aromatic or partially or fully hydrogenated. The cyclic ring systems can be substituted at will. Suitable substituents are, for example, $C_1$–$C_6$-alkyl, $C_1$–$C_4$-haloalkyl, $C_1$–$C_4$-alkoxy, halogen, cyano, nitro, hydroxyl, thionyl, sulfoxyl, sulfonyl, $C_1$–$C_4$-alkylsulfonyl, amino, $C_1$–$C_4$-alkylamino and di-$C_1$–$C_4$-alkylamino.

Preference is given to cyclic ring systems from the group consisting of $C_1$–$C_6$-cycloalkyl, phenyl, a 5- to 6-membered heterocyclic, saturated or unsaturated radical containing one to three heteroatoms selected from the group consisting of O, N and S. each of which may be substituted as mentioned above.

Particular preference is given to $C_1$–$C_6$-cycloalkyl and phenyl which may be substituted as mentioned above.

A very particularly preferred cyclic ring system is phenyl which may be substituted as mentioned above.

$R^2$, $R^3$ independently of one another [lacuna] $C_1$–$C_6$-alkyl as mentioned above or $C_3$–$C_6$-cycloalkyl, preferably $C_1$–$C6$-alkyl.

EXAMPLES

Example 1

3-Ethoxyacryloyl Chloride

At 35° C., 110 g (1.1 mol) of phosgene are introduced into a solution of 72 g (1 mol) of ethyl vinyl ether in 100 g of toluene over a period of 1.5 h. The mixture is subsequently stirred at 60° C. for 4 hours. During the entire reaction time, phosgene and ethyl vinyl ether are recondensed into the reaction mixture using a dry-ice condenser at −78° C. The solution is subsequently stripped of phosgene and room temperature, and the solvent is removed by distillation. Vacuum distillation at 36° C./0.4 mbar gives 88 g (66%) of the product of value.

Example 2
3-Isobutoxyacryloyl Chloride 100 g (1 mol) of isobutyl vinyl ether are initially charged in a 2 l stirred apparatus and heated to 50–55° C. 1024 g (10.4 mol) of phosgene are subsequently introduced over a period of 21 h, and 900 g (9 mol) of isobutyl vinyl ether are added dropwise over a period of 19 h. After an extra reaction time of 0.5 hours, the reaction mixture is heated to 80° C. with nitrogen stripping to eliminate hydrogen chloride. The low-boilers are then distilled off via a 15 cm Vigreux column, and the residue is analyzed by gas chromatography. This gives 1551 g (80%) of crude isobutoxyacrylolyl chloride (calc. 100%).

Example 3
3-Cyclohexyloxyacryloyl Chloride 50 g (0.5 mol) of phosgene are condensed into a stirred apparatus fitted with −78° C.-cooling. Over a period of 3 hours, 50.5 g (0.4 mol) of cyclohexyl vinyl ether are subsequently added dropwise at 20° C. The mixture is then stirred at 50° C. for 5 hours. The excess phosgene is flushed out with nitrogen, and the crude product is worked up by distillation. At 110° C./2.5 mbar, 66.4 g (88%) of the product of value were obtained.

Example 4
Isobutyl Isobutoxyacrylate 100 g (1.0 mol) of isobutyl vinyl ether are initially charged in a 500 ml stirred apparatus and heated to 50–55° C. 113 g (1.15 mol) of phosgene are subsequently introduced over a period of 11 h. After an extra reaction time of 1.5 h, the reaction mixture is stripped phosgene free at 50–55° C. by introduction of nitrogen. The mixture is subsequently allowed to cool to room temperature, and and [sic] 60.7 g (0.82 mol) of isobutanol are added dropwise. After the addition has ended, the resulting reaction mixture is rectified. This gives 150.4 g (75%) of isobutyl 3-isobutoxyacrylate of b.p. 97° C. at 2.5 mbar.

Example 5
5-Hydroxy-1-methylpyrazole from Methyl 3-methoxyacrylate and Monomethylhydrazine (35%)

In a 250 ml flask, 106.2 g (0.808 mol) of 35% strength aqueous monomethylhydrazine and 47.82 g (0.404 mol) of methyl 3-methoxyacrylate are simultaneously metered at 25° C. and over a period of 25 min into 70 g of methanol. The reaction mixture is stirred at 25° C. for 2 hours and then analyzed by gas chromatography. The yield is 95% at 100% conversion (in each case based on methyl 3-methoxyacrylate).

Isomer ratio: (5-hydroxy isomer:3-hydroxy isomer)≧200:1

Example 6
5-Hydroxy-1-methylpyrazole from Isobutyl 3-isobutoxyacrylate and Monomethylhydrazine (35%)

In a 0.75 l reactor, 287.5 g (2.18 mol) of 35% strength aqueous monomethylhydrazine and 175.2 g (0.875 mol) of isobutyl 3-isobutoxyacrylate are simultaneously metered at 25° C. and over a period of 1.5 hours into 202 g of methanol. The reaction mixture is stirred at 25° C. for 6.75 hours, then cooled to 5° C. for 16 hours and subsequently analyzed by gas chromatography. The yield is 88% at 98% conversion (in each case based on isobutyl isobutoxyacrylate).

Isomer ratio: (5-hydroxy isomer:3-hydroxy isomer)≧300:1

Example 7
3-Hydroxy-1-methylpyrazole from Methyl 3-methoxyacrylate and Monomethylhydrazine (35%)

In a 250 ml flask, 70 g of methanol and 60.5 g (0.46 mol) of 35% strength aqueous monomethylhydrazine are initially charged at 25° C. At the same temperature, 47.8 g (0.40 mol) of methyl 3-methoxyacrylate are metered in over a period of 25 min. By parallel addition of 17% strength aqueous NaOH solution, the pH of the reaction mixture during the metered addition of the methyl methoxyacrylate and during the extra stirring time (6 hours) is maintained at 12. Over this period of time, 97.5 g of NaOH solution are consumed. The yield is 75% at 100% conversion.

Isomer ratio: (3-hydroxy isomer:5-hydroxy isomer)≧15:1

Example 8
1-Ethoxycarbonylmethyl-5-hydroxypyrazole from Methyl 3-methoxyacrylate and Ethyl Hydrazineacetate Hydrochloride In a 2 l round-bottomed flask, 85.5 g (0.55 mol) of ethyl hydrazineacetate hydrochloride are initially charged in 770 ml of methanol at 25° C. At 60–65° C., 63.8 g (0.55 mol) of methyl 3-methoxyacrylate are metered in over a period of 1.25 hours. After the addition has ended, the mixture is refluxed for 2 hours and subsequently adjusted to a pH of 5 using 30% strength methanolic sodium methoxide solution. The reaction mixture is subsequently analyzed by gas chromatography. The yield is 85% at 100% conversion.

Using the processes described above, the compounds below were prepared in a similar manner.

| Constitution | Physical data; 1H NMR data |
|---|---|
| pyrazole with N-Et, OH | m.p. 94° C.<br>1H NMR (d6-DMSO): 1.3 (t, 3H), 3.9 (q, 2 H), 5.3 (d, 1H), 7.3 (d, 1H), 10.4 (brd., 1H). |
| pyrazole with N-nPr, OH | b.p. (1 mbar): 114° C.<br>1H NMR (d6-DMSO): 0.8 (t, 3H), 1.6 (m, 2 H), 3.7 (t, 2H), 5.3 (d, 1H), 7.0 (d, 1H). |
| pyrazole with N-nBu, OH | b.p. (0.5 mbar): 107–108° C.<br>1H NMR (d6-DMSO): 0.9 (t, 3H), 1.2 (m, 2 H), 1.7 (m, 2H), 3.8 (t, 2H), 5.2 (d, 1H), 7.0 (d, 1H), 9.1 (brd., 1H). |
| pyrazole with N-iBu, OH | b.p. (2 mbar): 135° C.<br>1H NMR (d6-DMSO): 0.9 (d, 6H), 2.1 (sept., 1H), 3.5 (d, 2H), 5.2 (d, 1H), 7.0 (d, 1H), 10.6 (brd., 1H). |

-continued

| Constitution | Physical data; 1H NMR data |
|---|---|
| 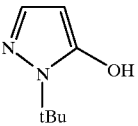 | 1H NMR (d6-DMSO): 1.5 (s, 9H), 5.3 (d, 1 H), 7.0 (d, 1H), 10.6 (brd., 1H). |
| 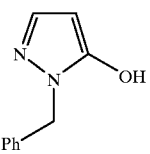 | 1H NMR (d6-DMSO): 5.1 (s, 2H), 5.3 (s, 1 H), 7.1–7.3 (m, 6H), 11.1 (brd., 1H). |
| 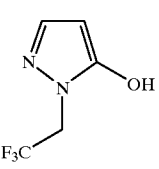 | 1H NMR (d6-DMSO): 4.7 (q, 2H), 5.4 (d, 1 H), 7.3 (d, 1H9, 11.4 (brd., 1H). |
| 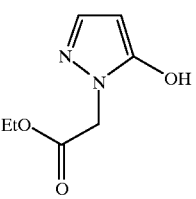 | 1H NMR (d6-DMSO): 1.2 (t, 2H), 4.1 (q, 2 H), 4.7 (s, 2H), 5.3 (d, 1H), 7.2 (d, 1H), 11.2 (brd., 1H). |
| 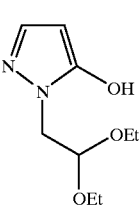 | 1H NMR (d6-DMSO): 1.0 (t, 6H), 3.3 (m, 2 H), 3.6 (m, 2H), 3.9 (d, 2H), 4.7 (t, 1H), 5.3 (d, 1H), 7.1 (d, 1H), 11.0 (brd., 1H). |
| 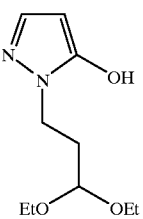 | 1H NMR (d6-DMSO): 1.1 (t, 6H), 1.9 (m, 2 H), 3.4 (m, 2H), 3.6 (m, 2H), 3.9 (m, 2H), 4.5 (m, 1H), 5.3 (d, 1H), 7.1 (d, 1H), 11.0 (brd., 1H). |

The 1-substituted 5- or 3-hydroxypyrazoles prepared by the process according to the invention are useful precursors for preparing, for example, crop protection agents, such as herbicides. Herbicides disclosed in WO 96/26206 are, for example,

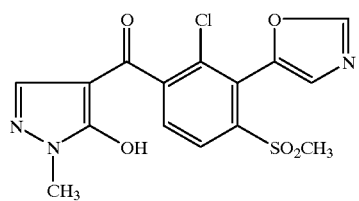 or

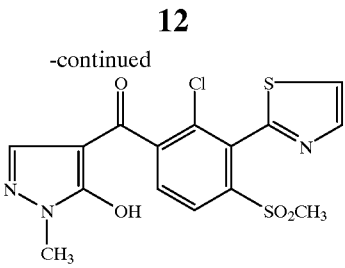

We claim:

1. A process for preparing a 1-substituted 5- and/or 3-hydroxypyrazole of the formulae I and II, respectively

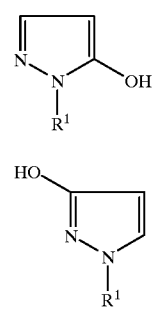

in which $R^1$ is $C_1$–$C_6$-alkyl, $C_2$–$C_6$-alkenyl, $C_2$–$C_6$-alkynyl, $C_3$–$C_6$-cycloalkyl or $C_1$–$C_4$-alkoxy, where these groups may be substituted by halogen, $C_1$–$C_4$-alkoxy, phenoxy, $C_1$–$C_6$-alkoxycarbonyl, $C_1$–$C_6$-alkylthiocarbonyl or by a cyclic ring system having 3–14 ring atoms, which comprises reacting c) an alkyl vinyl ether of the formula V

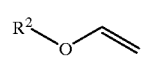

in which $R^2$ is $C_1$–$C_6$-alkyl or $C_3$–$C_6$-cycloalkyl with phosgene VIa, "diphosgene" VIb or "triphosgene" VIc

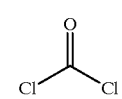

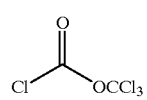

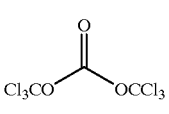

to give an acyl chloride of the formula VII

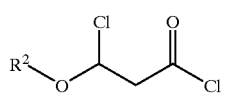

d) converting this by elimination of hydrogen chloride into the corresponding 3-alkoxyacryloyl chloride of the formula VIII

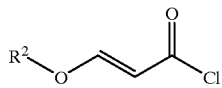

and e) esterifying this with an alcohol of the formula IX

in which $R^3$ is $C_1$–$C_6$-alkyl or $C_3$–$C_6$-cycloalkyl to give the corresponding alkyl 3-alkoxyacrylate of the formula III, and reacting said alkyl 3-alkoxyacrylate of the formula III

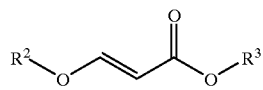

with a hydrazine of the formula IV

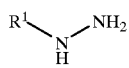

in which $R^1$ is as defined above a) at a pH of 6–11 to give 5-hydroxypyrazoles of the formula I or b) at a pH of 11–14 to give 3-hydroxypyrazoles of the formula II.

2. A process as claimed in claim 1, wherein the reaction in step a) is carried out at from −30° C. to 100° C.

3. A process as claimed in claim 1, wherein the reaction is carried out in the presence of a base.

4. A process as claimed in claim 1, wherein the base used is an alkali metal hydroxide, alkaline earth metal hydroxide or tertiary amine.

5. A process as claimed in claim 2, wherein a solvent is initially charged and the alkyl 3-alkoxyacrylate III and the hydrazine IV are simultaneously metered into the solvent.

6. A process as claimed in claim 5, wherein the solvent used is water, an alcohol, an ether or a mixture of these.

7. A process as claimed in claim 1, wherein the reaction in step b) is carried out at from −30° C. to 100° C.

8. A process as claimed in claim 7, wherein the reaction is carried out in the presence of a base.

9. A process as claimed in claim 8, wherein the base used is an alkali metal hydroxide, alkaline earth metal hydroxide, a tertiary amine or a mixture of these.

10. A process as claimed in claim 1, wherein the reaction in step c) is carried out at from −78° C. to 100° C.

11. A process as claimed in claim 1, wherein the alkyl vinyl ether V is reacted with phosgene VIa, diphosgene VIb or triphosgene VIc in a molar ratio of from 0.1:1 to 1:1.

12. A process as claimed in claim 1, wherein the reaction in step d) is carried out at from 30° C. to 80° C.

13. A process as claimed in claim 1, wherein the esterification in step e) is carried out at from −20° C. to 80° C.

* * * * *

UNITED STATES PATENT AND TRADEMARK OFFICE
CERTIFICATE OF CORRECTION

PATENT NO. : 6,392,058 B1
DATED : May 21, 2002
INVENTOR(S) : Maywald et al.

It is certified that error appears in the above-identified patent and that said Letters Patent is hereby corrected as shown below:

Title page,
Item [54], the title should read: -- METHOD FOR PRODUCING 1-SUBSTITUTED 5- OR 3-HYDROXYPYRAZOLES --

Signed and Sealed this

Fifteenth Day of October, 2002

*Attest:*

*Attesting Officer*

JAMES E. ROGAN
*Director of the United States Patent and Trademark Office*